United States Patent [19]

Chen

[11] Patent Number: 5,015,662

[45] Date of Patent: May 14, 1991

[54] ANTHELMINTIC BIOCONVERSION PRODUCTS

[75] Inventor: Shieh-Shung T. Chen, Morganville, N.J.

[73] Assignee: Merck & Co., Inc., Rahway, N.J.

[21] Appl. No.: 259,563

[22] Filed: Oct. 18, 1988

[51] Int. Cl.$^5$ ............... C07D 493/222; A61K 31/35
[52] U.S. Cl. ................................. 514/450; 549/264
[58] Field of Search .................. 549/264; 574/450

[56] References Cited

U.S. PATENT DOCUMENTS 4,666,937 5/1987 Goegelmann et al. ............ 549/264
4,831,016 5/1989 Mrozik et al. ..................... 549/264

FOREIGN PATENT DOCUMENTS 170006 3/1985 European Pat. Off. ............ 549/264
214731 3/1987 European Pat. Off. ............ 549/264

Primary Examiner—Richard L. Raymond
Assistant Examiner—Mark W. Russell
Attorney, Agent, or Firm—David L. Rose; Joseph F. DiPrima

[57] ABSTRACT

There are disclosed new compounds with significant antiparasitic activity which are prepared by fermenting compounds identified as LL-F28249 in a novel microorganism identified as *Streptomyces avermitilis* MA-5542. The LL-F28249 compounds are modified by the microorganism by hydroxylation of the 25-position terminal methyl group. The compounds are significant antiparasitic and anthelmintic agents and compositions for that use are also disclosed.

5 Claims, No Drawings

ANTHELMINTIC BIOCONVERSION PRODUCTS

BACKGROUND OF THE INVENTION

In European Patent 170006, there are disclosed a series of compounds identified as LL-F28249. Of the 14 compounds disclosed, 13 have a milbemycin type macrocyclic ring system with a branched unsaturated alkyl side chain of from 4 to 7 carbon atoms at the 25-position. The compounds are best described in the following structural formulae:

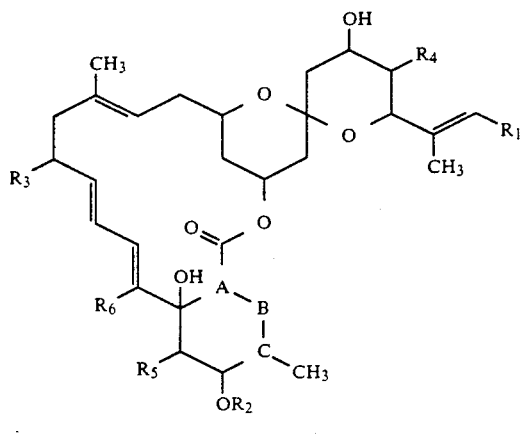

LL-F28249α-μ

The LL-F28249 compounds are prepared by the fermentation of *Streptomyces cyaneogriseus* sub sp. non-cyanogenous NRRL15773. The morphological characteristics of NRRL15773 are completely described in the above-cited European patent along with processes for the preparation of such compounds.

SUMMARY OF THE INVENTION

The instant invention is concerned with the preparation of novel compounds which are prepared by the bioconversion of known LL-F28249 compounds in a previously unknown microorqanism, *Streptomyces avermitilis* MA-5542. Thus, it is an object of this invention to describe such novel compounds. It is a further object of this invention to describe the process used to prepare such novel compounds. It is a still further object to describe the novel microorganism used to prepare such compounds. Another object is to describe the use of such compounds as anthelmintic and parasiticidal agents. Additional objects will become apparent from a reading of the following description.

DESCRIPTION OF THE INVENTION

The compounds of the instant invention are best realized in the following structural formulae:

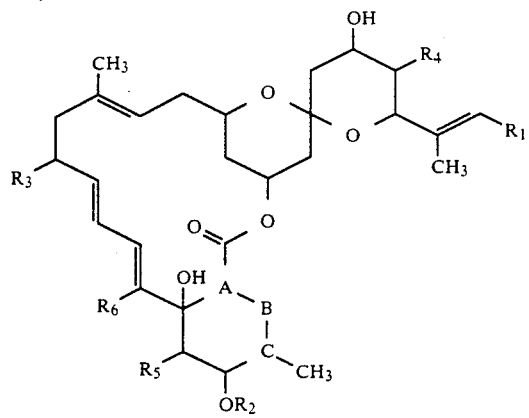

The LL-F28249 compounds are prepared by the fermentation of *Streptomyces cyaneoqriseus* sub sp. non-cyanogenous NRRL15773. The morphological characteristics of NRRL15773 are completely described in the above-cited European patent along with processes for the preparation of such compounds.

SUMMARY OF THE INVENTION

The instant invention is concerned with the preparaton of novel compounds which are prepared by the bioconversion of known LL F28249 compounds in a previously unknown microorqanism, *Streptomyces avermitilis* MA- 5542. Thus, it is an object of this invention to describe such novel compounds. It is a further object of this invention to describe the process used to prepare such novel compounds. It is a still further object to describe the novel microorganism used to prepare such compounds.

DESCRIPTION OF THE INVENTION

In accordance with this invention, novel substances are described which are prepared by growing under controlled conditions a strain of microorqanism identified as *Streptomyces avermitilis* and including in the fermentation broth a substrate which is an LL-F28249 compound. This microorganism is identified in the Merck Culture Collection as MA-5542 and is publicly available from the American Type Culture Collection at 12301 Parklawn Drive, Rockville, MD 20852 under the accession number ATCC 53814.

The morphological and cultural characteristics of Streptomyces avermitilis MA 5542, ATCC 53814 are as follows:

CULTURAL CHARACTERISTICS OF MA5542 *STREPTOMYCES AVERMITILIS*

OATMEAL AGAR

Vegetative Growth: Reverse: Hyaline Obverse:
Flat colonies, entire edges.
Aerial Mycelium:
Abundant, powdery, greyish-white
Soluble Pigment: Yellow brown

CZAPEK-DOX AGAR (SUCROSE NITRATE AGAR)

Vegetative Growth: Good, colorless. Clear zones around periphery of growth.
Aerial Mycelium: Abundant, greyish-white.
Soluble Pigment: Slight browning.

EGG ALBUMIN AGAR

Vegetative Growth: Yellow, flat growth.
Aerial Mycelium: None.
Soluble Pigment: None.

GLYCEROL ASPARAGINE AGAR

Vegetative Growth: Reverse: Off white. Obverse: Poor growth, off white flat colonies, erose edges.
Aerial Mycelium: Sparse, off white.
Soluble Pigment: None.

INORGANIC SALTS STARCH AGAR

Vegetative Growth: Very poor, translucent flat colonies, irregular edges. Slight degree of clearing of medium beneath areas of growth.
Aerial Mycelium: None.
Soluble Pigment: None.

NUTRIENT TYROSINE AGAR

Vegetative Growth: Reverse: Dark brown to black. Obverse: Same.
Aerial Mycelium: None.
Soluble Pigment: Dark brown.
Decomposition of tyrosine: None.

SKIM MILK AGAR

Vegetative Growth: Mousey brown.
Aerial Mycelium: Abundant, greyish white.
Soluble Pigment: Dark brown.
Hydrolysis of Casein: Good.

YEAST EXTRACT MALT EXTRACT AGAR

Vegetative Growth: Reverse: Tan brown to light brown. Obverse: Yellow growth, erose edges. Well sporulated colonies displaying sectoring.
Aerial Mycelium: Sparse to abundant, blue-green with hint of grey.
Soluble Pigment: Brown yellow.

NUTRIENT AGAR

Vegetative Growth: Tannish brown.
Aerial Mycelium: Sparse, greyish.
Soluble Pigment: Light brown.

NUTRIENT STARCH AGAR

Vegetative Growth: Tannish brown.
Aerial Mycelium: Sparse, grey.
Soluble Pigment: Light brown.
Hydrolysis of Starch: Good.

TOMATO PASTE OATMEAL

Vegetative Growth: Poor to none.

GELATIN STABS

Vegetative Growth: Brown ring.
Aerial Mycelium: None.
Soluble Pigment: Brown.
Liquefaction of gelatin: None.

PEPTONE-IRON-YEAST EXTRACT AGAR SLANTS

Vegetative Growth: Greyish brown.
Aerial Mycelium None
Soluble Pigment: Dark brown to black
Melanin: Positive
$H_2$: Positive

CZAPEK-DOX AGAR SLANTS

Vegetative Growth: Colorless
Aerial Mycelium: None.
Soluble Pigment: None.

TRYPTONE YEAST EXTRACT BROTH

Soluble Pigment: Dark brown.

CARBON UTILIZATION

Pridham-Gottlieb basal medium +1% carbon source; graded according to standards in "Methods for Characterization of *Streptomyces* Species", *International Journal of Systemic Bacteriology*, Vol 16, No. 3, July 1966 pps. 313-340.

| | |
|---|---|
| NS (No Carbon Source) | no growth |
| alpha-D-Glucose (Positive Control) | no growth |
| D-Arabinose | — |
| L-Arabinose | — |
| D-Fructose | — |
| L-Glucose | — |
| Inositol | — |
| alpha-D-Lactose | — |
| beta-D-Lactose | — |
| D-Maltose | — |
| D-Mannitol | — |
| D-Mannose | — |
| L-Mannose | — |
| D-Raffinose | — |
| L-Rhamnose | — |
| Sucrose | — |
| D-Xylose | — |
| L-Xylose | — |

ALL READINGS TAKEN AFTER 3 WEEKS INCUBATION 28C.

Microscopic characteristics—(1000x, dark field phase)—culture grows as branching fialmentous mycelium, 0.6m diameter. Spores are borne in tightly coiled chains that form as side branches. Sporulation is evident on oatmeal, Czapek Dox, glycerol asparagine, skim milk, and yeast malt agars.

The culture MA-5542 is a valine-negative strain of *Streptomyces avermitilis* and is significantly different from other *Streptomyces avermitilis* strains in that MA-5542 produces only small amounts of avermectin compounds (formerly referred to as C-076 compounds).

The instant compounds are produced during the aerobic fermentation of suitable aqueous nutrient -media under conditions described hereinafter, with a producing strain of Streptomyces avermitilis MA- 5542, ATCC 53814. Aqueous media such as those used for the production of many antibiotic substances are suitable for use in the process for the production of these macrocyclic compounds.

Such nutrient media contain sources of carbon and nitrogen assimilable by the microorqanism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 1 and 10 g/l in the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, and the like, are readily assimilable by *Streptomyces avermitilis* MA- 5542, ATCC 53814 in the production of the instant compounds. The various sources of nitrogen can be used alone or in combination in amounts ranging from 1 to 5 g/l in the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of *Streptomyces avermitilis*, ATCC 53814:

| Composition of Media | |
|---|---|
| Medium 1 | |
| Dextrose | 20 g. |
| Peptone | 5 g. |
| Meat Extract | 5 g. |
| Primary Yeast | 3 g. |
| NaCl | 5 g. |
| CaCO$_3$ (after pH adjustment) | 3 g. |
| Distilled Water | 1000 ml. |
| pH 7.0 | |
| Medium 2 | |
| Tomato Paste | 20 g. |
| Modified Starch (CPC) | 20 g. |
| Primary Yeast | 10 g. |
| CoCl$_2$6H$_2$O | 0.005 g. |
| Distilled Water | 1000 ml. |
| pH 7.2-7.4 | |
| Medium 3 (Slant Medium) | |
| Dextrose | 10.0 g. |
| Bacto Asparagine | 0.5 g. |
| K$_2$HPO$_4$ | 0.5 g. |
| Bacto Agar | 15.0 g. |
| Distilled Water | 1000 ml. |
| pH 7.0 | |
| Medium 4 (Seed Medium) | |
| Soluble Starch | 10.0 g. |
| Ardamine pH | 5.0 g. |
| NZ Amine E | 5.0 g. |
| Beef Extract | 3.0 g. |
| MgSO$_4$7H$_2$O | 0.5 g. |
| Cerelose | 1.0 g. |
| Na$_2$HPO$_4$ | 0.190 g. |
| KH$_2$PO$_4$ | 0.182 g. |
| CaCO$_3$ | 0.5 g. |
| Distilled Water | 1000 ml. |
| ph 7.0-7.2 | |
| Medium 5 | |
| Tomato Paste | 40.0 g. |
| Oat Flour | 10.0 g. |
| Cerelose | 10.0 g. |
| Corn Steep Liquor | 5.0 g. |
| Trace Element Mix | 10.0 ml. |
| Distilled Water | 1000 ml. |

| -continued | |
|---|---|
| Composition of Media | |
| pH 6.8 | |
| Trace Element Mix | 1000 ml. |
| FeSO$_4$.7H$_2$O | 1000 mg. |
| MnSO$_4$.4H$_2$O | 1000 mg. |
| CuCl$_2$.2H$_2$O | 25.0 g. |
| CaCl$_2$ | 100.0 mg. |
| H$_2$BO$_3$ | 56.0 mg. |
| (NH$_4$)$_2$MoO$_4$.4H$_2$O | 10.0 mg. |
| ZnSO$_4$.7H$_2$O | 200.0 mg. |
| Distilled Water | 1000 ml. |
| pH | |
| Medium 6 | |
| CPC Industrial Starch Modified (Available from CPC Corp.) | 40.0 g. |
| Distiller's Solubles | 7.0 g. |
| Autolyzed Yeast (Ardamine pH available from Yeast Products Inc.) | 5.0 g. |
| CoCl$_2$.6H$_2$O | 50.0 mg. |
| Distilled Water | 1000 ml. |
| pH 7.3 | |

The fermentation employing *Streptomyces avermitilis*, MA-5542 ATCC 53814 can be conducted at temperatures ranging from about 20° C. to about 40° C. For optimum results, it is most convenient to conduct these fermentations at a temperature in the range of from about 24° C. to about 30° C. Temperatures of about 27-28° C. are most preferred. The pH of the nutrient medium suitable for producing the instant compounds can vary from about 5.0 to 8.5 with a preferred range of form about 6.0 to 7.5.

The LL F28249 compounds are added to the fermentation of *Streptomyces avermitilis* MA- 5542 in quantities of from 0.1 to 1.0 g per liter of fermentation medium. It is preferred to use from 0.1 to 0.5 g per liter. The LL-F28249 compound may be added at any time during the fermentation cycle. The compounds may be added to the medium ingredients before the culture is added and the fermentation begins or they may be added during the course of the fermentation. In order that the cultures have sufficient time to effect the biotransformation, it is preferred that the LL-F28249 compounds be added to the fermentation before 50% of the cycle is completed, preferably before 25% of the cycle is completed.

Small scale fermentations are conveniently carried out by placing suitable quantities of nutrient medium in a flask employing known sterile techniques, inoculating the flask with either spores or vegetative cellular growth of *Streptomyces avermitilis* MA- 5542, ATCC 53814, loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Streptomyces avermitilis* MA-5542. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 rpm and about 50 to 500 liters per minute (CFM) of air.

The separation of the novel compound from the whole fermentation broth and the recovery of said compounds is carried out by solvent extraction and application of chromatographic fractionations with various chromatographic techniques and solvent systems.

The instant compounds have slight solubility in water, but are soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extract ions are desirable to achieve maximum recovery. The solvent removes the instant compound as well as other substances lacking the antiparasitic activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the combinations of solvents as the eluent. Thin layer, high pressure, liquid and preparative layer chromatography may be employed to detect the presence of, and to isolate the instant compounds. The use of the foregoing techniques as well as others known to those skilled in the art, will afford purified compositions containing the instant compounds. The presence of activity of physico-chemical characteristics. The structures of the instant compounds have been determined by detailed analysis of the various spectral characteristics of the compounds, in particular their nuclear magnetic resonance, mass, ultraviolet and infrared spectra.

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Tricho strongylus, Ostertagia, Nematodirus, Cooperia, Ascaris, Bunostomum, Oesophagostomum, Chabertia, Trichuris, Stongylus, Trichonema, Dictyocaulus, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly Musca domestica.

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and constant of the antiparasitic agent depending upon factors such as the type of host animal to be treated, the severity and type of infection and the weight of the host.

When the active compound is to be administer ed via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active compound or compounds are dissolved or suspended in the parenteral formulation for administration; such formulations generally contain from 0.55 to 5% by weight of the active compound.

Although the antiparasitic agents of this invention find their primary use in the treatment and/or prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection of infestation. Generally, good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given are required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

In using the compounds of this invention, the individual components may be isolated and purified and used in that form. Alternatively, mixtures more of the individual components may be used. It is not necessary to completely separate the various compounds obtained from the purification of the fermentation broth. Generally, there is obtained a mixture containing two or more of the compounds, but having other unrelated compounds excluded therefrom, and such mixture may be used for the prevention and treatment of parasitic diseases as described herein. Such a mixture generally will contain unequal proportions of substantial activity and the antiparasitic activity of the mixture can be accurately determined.

In addition, where the compounds are to be added to an animal s feed, it is possible to utilize the dried mycelial cake from the fermentation broth. The mycelia contain a preponderance of the activity and since the level of the activity of the mycelia can be determined, it can be added directly to the animal's feed.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The anthelmintic activity of the instant via the feed, a sample of the individual compound, a mixture of such compounds, a concentrated extract, and the like to a mouse which had been infected 3 days earlier with a gastrointestinal parasite. At 11, 12 and 13 days after the initiation of the medication, the feces of the mouse are examined for eggs, and on the next day the mouse is sacrificed and the number of worms present in the proximal portion of the small intestine are determined. An active compound is observed when there is a significant reduction of egg and worm counts when compared to infected, unmedicated controls.

The following examples are being provided in order that the instant invention may be more fully understood. Such examples are not to be construed as being limitative of the invention.

EXAMPLE 1

| Cultures: *Streptomyces avermitilis* MA5542, ATCC 53814. | |
|---|---|
| Medium: | g/l |
| A. | |
| Glucose | 20 |
| Hycase | 20 |
| Yeast extract | 20 |
| $KNO_3$ | 2.0 |
| $FeSO_4.7H_2O$ | 0.025 |
| NaCl | 0.5 |
| $MgSO_4$ | 0.5 |
| $MnSO_4$ | 0.005 |
| $ZnSO_4$ | 0.01 |
| $CaCl_2.2H_2O$ | 0.02 |
| pH 7.0 | |
| The medium is utilized for seed development and preservation of cultures. | |
| B. | |
| Cerelose | 45 |
| Peptonized milk | 24 |
| Ardamine pH | 2.5 |
| pH 7.0 | |
| The medium is utilized for transformation. | |

Substrate:

Compound LL-F28249α was prepared following the procedures described in European patent application number 0 170 006, published Feb. 5, 1986. Dimethylsulfoxide is used to solubilize the substrate for the addition.

Transformation:

The seed flasks were inoculated with a frozen vial of *Streptomyces avermitilis* MA -5542 and incubated on a rotary shaker (220 rpm) at 27° C. for 17 hrs. The transformation flasks (20 ml medium B in 250 ml Erlenmeyer flask) were inoculated with 1 ml of seed culture and incubated at 27° C. on a rotary shaker. The addition of the substrate (10 mg/flask) was made at 60 hr followed by harvest at 192 hr. With these conditions and average transformation yield of 2% Compound I was obtained from LL F28249α.

Isolation and Purification:

The transformation whole broth (20 ml) was clarified by centrifugation. The mycelial cake was washed with water. The collected wet cake was methanol extract was filtered and taken to dryness in vacuo. The residue was dissolved in methanol (2 ml) and filtered. The volume of the methanol solution was reduced to 0.5 ml under a stream of nitrogen. The sample was then separated by high performance liquid chromatography (HPLC) on a Whatman Partisil 10 ODS- 3 column developing at 3.5 ml/min with a 81/19 methanol/water system. The peak eluting at 10 min was collected. The solvent was removed in vacuo to yield 0.2 mg of Compound I which is identified by its nuclear magnetic resonance and mass spectra.

What is claimed is:

1. A compound having the formula:

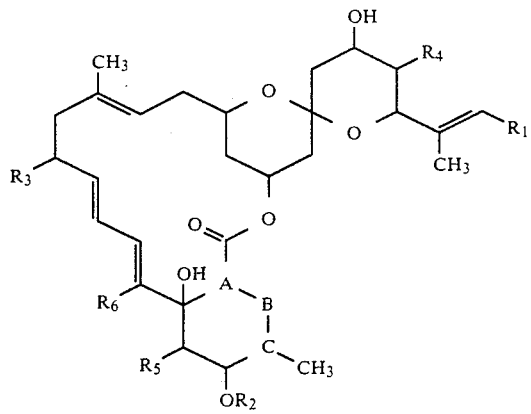

wherein $R_1$, $R_2$, $R_3$, $R_4$, $R_5$, $R_6$, A, B and C have the following meanings:

| $R_1$ | $R_2$ | $R_3$ | $R_4$ |
|---|---|---|---|
| $-CH(CH_3)CH_2OH$ | H | $CH_3$ | $CH_3$ |
| $-CH_2OH$ | H | $CH_3$ | $CH_3$ |
| $-CH_2OH$ | $CH_3$ | $CH_3$ | $CH_3$ |
| $-CH_2OH$ | $CH_3$ | $CH_3$ | $CH_3$ |
| $-CH(CH_3)CH_2OH$ | H | H | $CH_3$ |
| $-CH_2CH_2OH$ | H | $CH_3$ | $CH_3$ |
| $-CH(CH_3)CH_2OH$ | H | $CH_3$ | $CH_3$ |
| $-CH(CH_3)CH_2OH$ | H | $CH_3$ | $CH_2CH_3$ |
| $-CH(CH_3)CH_2OH$ | H | $CH_2CH_3$ | $CH_3$ |
| $-CH_2OH$ | $CH_3$ | $CH_3$ | $CH_3$ |
| $-CH(CH_3)CH_2OH$ | $CH_3$ | $CH_3$ | $CH_3$ |
| $-CH(CH_3)CH_2OH$ | $CH_3$ | $CH_3$ | $CH_3$ |

| $R_5$ | $R_6$ | $R_5 + R_6$ | A—B | B—C |
|---|---|---|---|---|
| | | $-O-CH_2-$ | CH—CH | CH=C |
| | | $-O-CH_2-$ | CH—CH | CH=C |
| | | $-O-CH_2-$ | CH—CH | CH=C |
| OH | $CH_2OH$ | | CH—CH | CH=C |
| | | $-O-CH_2-$ | CH—CH | CH=C |
| | | $-O-CH_2-$ | CH—CH | CH=C |
| | | $-O-CH_2-$ | C=CH | CH—CH |
| | | $-O-CH_2-$ | CH—CH | CH=C |
| | | $-O-CH_2-$ | CH—CH | CH=C |
| H | $CH_3$ | | CH—CH | CH=C |
| | | $-O-CH_2-$ | CH—CH | CH=C |
| H | $CH_3$ | | CH—CH | CH=C | and the compound

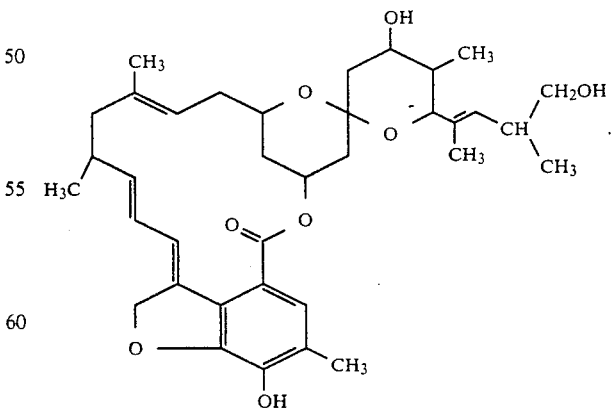

2. The compound of claim 1 wherein:
$R_1$ is $-CH(CH_3)CH_2OH$;
$R_2$ is H;
$R_3$ is $CH_3$;

$R_4$ is $CH_3$;
$R_5$ and $R_6$ together form $-O-CH_2-$;
A—B is —CH—CH; and
B—C is —CH=C—

3. A method for the treatment of parasitic infections in animals which comprises administering to such animals an effective amount of one or more compounds of claim 1.

4. A method for the treatment of pests on agricultural crops which comprises administering to such crops of the soil in which they grow, an effective amount of compound of claim 1.

5. A composition useful for the treatment of parasitic infections in animals or pests of agricultural crops which comprises an inert carrier and one or more compounds of claim 1.

* * * * *